United States Patent [19]

Matsuda et al.

[11] Patent Number: 5,047,520

[45] Date of Patent: Sep. 10, 1991

[54] 2'-ALKYLIDENEPYRIMIDINE NUCLEOSIDE DERIVATIVES, PROCESS FOR PRODUCTION THEREOF, AND USES THEREOF

[75] Inventors: Akira Matsuda; Tohru Ueda; Kenji Takenuki, all of Sapporo; Haruhiko Machida, Choshi, all of Japan

[73] Assignee: Yamasa Shoyu Kabushiki Kaisha, Chiba, Japan

[21] Appl. No.: 295,948

[22] PCT Filed: Mar. 17, 1988

[86] PCT No.: PCT/JP88/00278

§ 371 Date: Nov. 18, 1988

§ 102(e) Date: Nov. 18, 1988

[87] PCT Pub. No.: WO88/07049

PCT Pub. Date: Sep. 22, 1988

[30] Foreign Application Priority Data

Mar. 19, 1987 [JP] Japan ................................ 62-65405
Jan. 30, 1988 [JP] Japan ................................ 63-20032

[51] Int. Cl.$^5$ .................... A01N 43/04; A61K 31/70; C07H 17/02; C07H 15/12
[52] U.S. Cl. ......................................... 536/23; 536/27
[58] Field of Search .................. 536/23, 27; 514/49, 514/50, 51

[56] References Cited

PUBLICATIONS

Beres et al., J. Med. Chem., 1986, 29, 1243–1249.

Primary Examiner—Robert A. Wax
Assistant Examiner—F. Tsung
Attorney, Agent, or Firm—Wenderoth, Lind & Ponack

[57] ABSTRACT

Disclosed are novel 2'-alkylidenepyrimidine nucleoside derivatives represented by formula [I]:

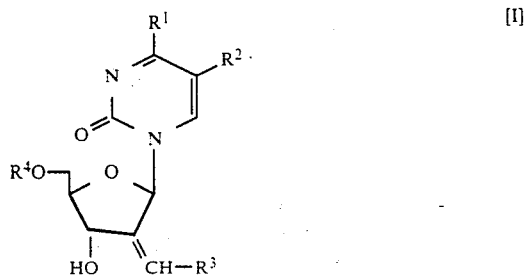

wherein $R^1$ is an amino gorup or a hydroxy group, $R^2$ is a hydrogen atom, a halogen atom or a lower alkyl group, $R^3$ is a hydrogen atom or a lower alkyl group, and $R^4$ is a hydrogen atom or a phosphate residue, or salts thereof.

These novel compounds can be produced from uridine or cytidine derivatives by alkylidenating the 2'-position in the sugar moiety thereof with Wittig's reagent.

Furthermore, the compounds have remarkable antiviral activities and therefore can provide novel antiviral agents.

11 Claims, No Drawings

2'-ALKYLIDENEPYRIMIDINE NUCLEOSIDE DERIVATIVES, PROCESS FOR PRODUCTION THEREOF, AND USES THEREOF

TECHNICAL FIELD

The present invention relates to novel compounds, 2'-alkylidenepyrimidine nucleoside derivatives, a process for the production thereof, and antiviral agents comprising the compounds as active ingredients.

BACKGROUND ART

In recent years, the development of preventives and remedies for various viral infections has attracted particular attention with the advance of researches into pathogenic viruses.

Antiviral agents for use in chemotherapy heretofore proposed for clinical purposes are idoxuridine, cytarabine, vidarabine, acyclovir and the like. (See, for example, Yutaka Mizushima and Terumasa Miyamoto, The Edition of 1986, "Konnichi no Chiryo-yaku (Present-Day Remedies), Kaisetsu to Binran (Explanation and Manual)", Nanko-do, pp. 47–50 (Mar. 10, 1986).)

Most of the above-mentioned drugs, however, have been accompanied by problems including limited clinical applicability due, for instance, to antiviral activity spectra, low absorption, poor solubility, easy decomposition, the advent of drug-fast virus strains, and various side effects. Accordingly, there has been an urgent demand for the development of novel antiviral agents.

A primary object of the present invention is to provide novel compounds having remarkable antiviral activities.

DISCLOSURE OF INVENTION

As a result of extensive research efforts for the development of novel compounds useful as antiviral agents, we have found that 2'-alkylidenepyrimidine nucleoside derivatives represented by the following formula [I] have excellent antiviral activities. On the basis of this finding, we have arrived at the present invention.

More particularly, the present invention relates to 2'-alkylidenepyrimidine nucleoside derivatives represented by formula [I]:

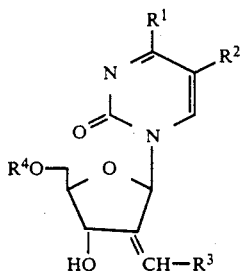

[I]

Wherein $R^1$ is an amino or hydroxy group, $R^2$ is a hydrogen or halogen atom or a lower alkyl group, $R^3$ is a hydrogen atom or a lower alkyl group, and $R^4$ is a hydrogen atom or a phosphate residue, and salts thereof.

This invention also relates to a process for producing 2'-alkylidenepyrimidine nucleoside derivatives represented by the above formula [I], which process comprises Steps (1), (2) and (3) set forth below (hereinafter referred to as "the first process". The first process illustrates inclusively the second, third and fourth processes described hereinlater.

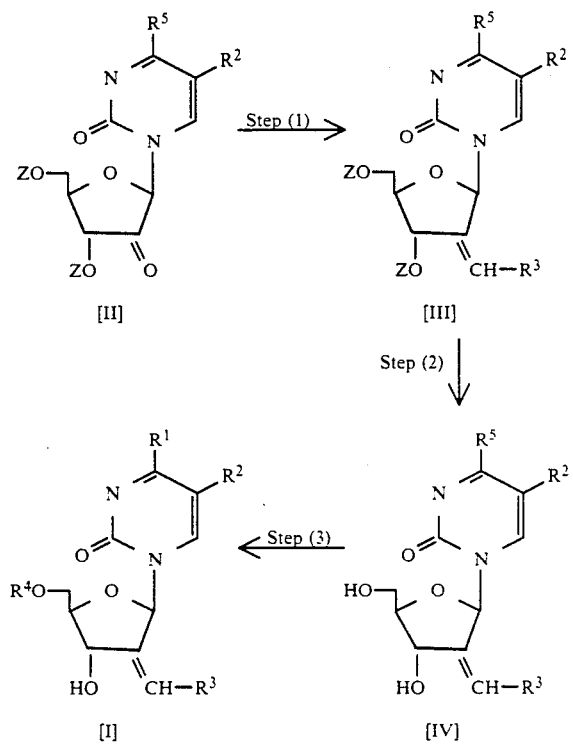

wherein $R^1$, $R^2$, $R^3$ and $R^4$ are as defined previously, $R^5$ is alkoxy, hydroxy, amino or acylamino ($-NHR^6$, $R^6$ being an acyl group), and Z is a hydroxy protecting group in the sugar moiety.

In the process shown above, Step (1) involves the alkylidenation of the 2'-position in the sugar moiety of a compound of formula [II] with Wittig's reagent, Step (2) involves the removal of the hydroxy protecting groups in the sugar moiety of a compound of formula [III] thus obtained, and Step (3) involves the hydrolysis or amination of the 4-position in the base moiety of a compound of formula [IV] resulting from Step (2) when $R^5$ is an alkoxy group, or the removal of the acyl protecting group when $R^5$ is an acylamino group, and the subsequent optional phosphorylation at the 5'-position in the sugar moiety irrespective of whether $R^5$ is an alkoxy, hydroxy, amino or acylamino group to obtain a compound of formula [I].

The present invention further relates to a process for producing 2'-alkylidenepyrimidine nucleoside derivatives represented by formula [I] shown earlier, which process comprises the following Steps (1), (2) and (3) (hereinafter referred to as "the second process").

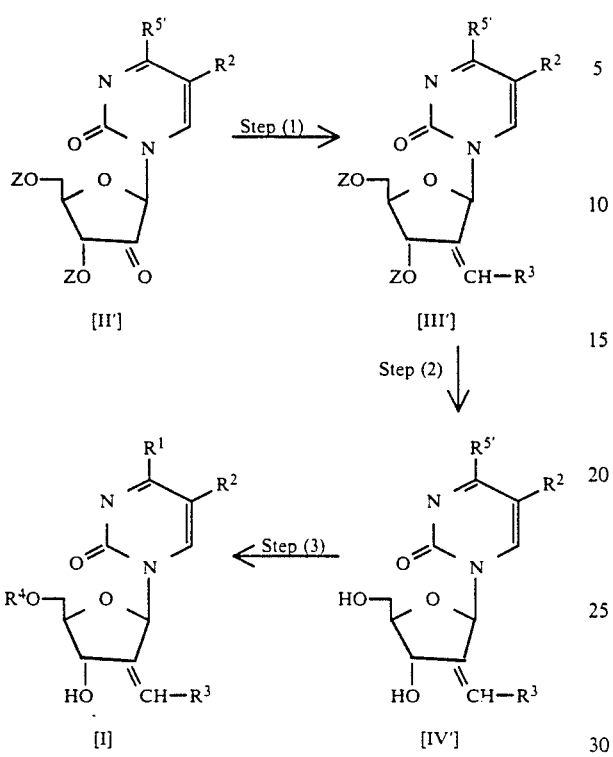

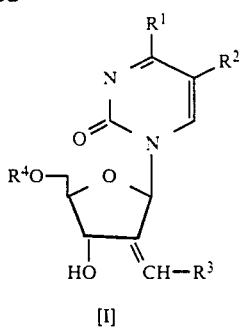

wherein $R^1$, $R^2$, $R^3$, $R^4$ and Z are as defined hereinbefore.

In the above process, Step (1) is the same reaction step as that in the first process, and Step (2) involves the removal of the hydroxy protecting groups in the sugar moiety and the subsequent optional phosphorylation at the 5'-position in the sugar moiety to obtain a compound of formula [I].

Furthermore, the present invention relates to a process for producing 2'-alkylidenepyrimidine nucleoside derivatives represented by formula [I''''] shown below, which process comprises the following Steps (1), (2) and (3) (hereinafter referred to as "the fourth process").

wherein $R^1$, $R^2$, $R^3$, $R^4$ and Z are as defined previously, and $R^{5'}$ is an alkoxy group.

In this process, Steps (1) and (2) are the same reaction steps as those in the aforementioned first process, and Step (3) involves the hydrolysis or amination of the 4-position in the base moiety and the subsequent optional phosphorylation at the 5'-position in the sugar moiety to obtain a compound of formula [I].

The present invention still further relates to a process for producing 2'-alkylidenepyrimidine nucleoside derivatives of formula [I] shown above, which process comprises the following Steps (1) and (2) (hereinafter referred to as "the third process").

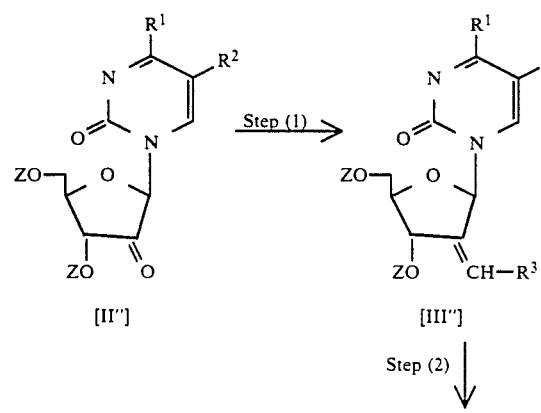

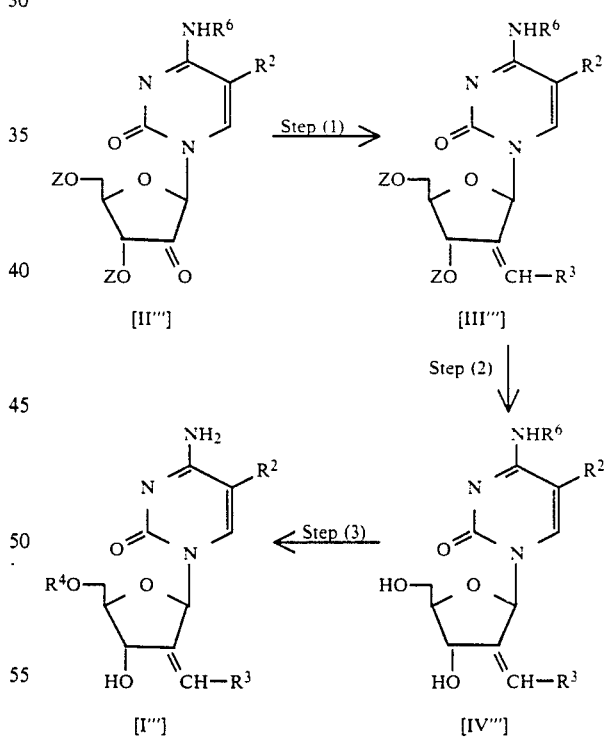

wherein $R^2$, $R^3$, $R^4$ and Z are as defined hereinbefore, and $R^6$ is an acyl group.

In the above process, Steps (1) and (2) are the same reaction steps as those in the first process, and Step (3) involves the removal of the acyl group represented by $R^6$ and the subsequent optional phosphorylation at the 5'-position in the sugar moiety to obtain a compound of formula [I'''].

The present invention, in another aspect thereof, relates to an antiviral agent comprising an effective amount of 2'-alkylidenepyrimidine nucleoside derivatives of the above shown formula [I] or salts thereof and a pharmaceutically acceptable carrier or adjuvant.

The present invention, in still another aspect thereof, relates to a method for the treatment of viral infections in a subject which comprises administering a therapeutically effective amount of the antiviral agent described above to said subject.

BEST MODE FOR CARRYING OUT THE INVENTION

Hereinafter, the present invention will be set forth in detail.

COMPOUND OF THE PRESENT INVENTION

The 2'-alkylidenepyrimidine nucleoside derivatives according to the present invention are represented by formula [I] shown hereinbefore.

$R^1$, $R^2$, $R^3$ and $R^4$ in the formula are as defined previously. The term "lower alkyl" means alkyl of 1 to 8 carbon atoms. Specific examples of the lower alkyl groups represented by $R^2$ and $R^3$ are those having 1 to 3 carbon atoms, more specific examples being methyl, ethyl, propyl and isopropyl. Examples of the halogen atom represented by $R^2$ are chlorine, fluorine, bromine, and iodine.

Typical examples of the compounds of the present invention include nucleosides such as 2'-methylidene-2'-deoxyuridine, 2'-methylidenethymidine, 2'-ethylidenethymidine, 2'-methylidene-2'-deoxycytidine, 2'-methylidene-2'-deoxy-5-fluorouridine, 2'-methylidene-2'-deoxy-5-chlorouridine, 2'-methylidene-2'-deoxy-5bromouridine, and 2'-methylidene-2'-deoxy-5-iodouridine, and 5'-phosphates thereof.

Among these nucleosides of the present invention, a group of compounds of formula [I] wherein $R^2$ is a hydrogen or halogen atom or a methyl group and $R^3$ is a hydrogen atom have a high antiviral activity against herpes simplex virus (HSV).

The compounds of the present invention also include salts thereof. Examples of such salts are any pharmaceutically acceptable salts, such as acid addition salts including hydrochloride and sulfate in the case where $R^4$ in the aforementioned formula [I] is a hydrogen atom, and alkali metal salts including sodium, potassium and lithium salts, alkaline earth metal salts including calcium salt, or ammonium salt in the case where $R^4$ is a phosphate residue.

PRODUCTION OF THE COMPOUNDS OF THE PRESENT INVENTION

The compounds of the present invention are novel compounds, and can be produced by the second to fourth processes set forth hereinbefore when $R^1$ in formula [I] is an amino group, while by the second and third processes when $R^1$ is a hydroxy group.

The reaction steps in the respective processes will be described below in detail.

PREPARATION OF THE STARTING COMPOUNDS

The pyrimidine nucleoside derivatives used in the process of the present invention as starting compounds are represented by formula [II'], [II"] or [II'"] shown earlier.

$R^1$, $R^2$, $R^{5'}$, $R^6$ and Z in the formulae are as defined previously. Specific examples of the alkoxy group represented by $R^{5'}$ are lower alkoxy groups having 1 to 3 carbon atoms, more specific examples being methoxy, ethoxy and propoxy. Examples of the acyl group represented by $R^6$ are aliphatic acyl groups such as acetyl, chloroacetyl, dichloroacetyl, trichloroacetyl, trifluoroacetyl, methoxyacetyl, propionyl, n-butyryl, isobutyryl, (E)-2-methyl-2-butenoyl, pentanoyl and pivaloyl, and aromatic acyl groups such as benzoyl, o-(dibromomethyl)benzoyl, p-phenylbenzoyl, 2,4,6-trimethylbenzoyl, p-toluoyl, p-anisoyl, p-halobenzoyl, p-nitrobenzoyl, and p-methoxybenzoyl. Further, the protecting group represented by Z may be any of those customarily used as hydroxy protecting groups, for example, acyl groups such as acetyl, propionyl, butyryl, benzoyl, and naphthoyl; acetal- or ketal-type protecting groups such as ethylidene, propylidene, isopropylidene, benzylidene, cyclohexylidene, cyclopentylidene, methoxymethylidene, ethoxymethylidene, and dimethoxymethylidene; aralkyl groups such as benzyl, p-methoxybenzyl, 3,4-dimethoxybenzyl, diphenylmethyl, triphenylmethyl, α- or β-naphthylmethyl, and α-naphthyldiphenylmethyl; and silyl groups such as trimethyldiisopropylsilyl, t-butyldimethylsilyl, methyldiisopropylsilyl, triisopropylsilyl, and tetraisopropyldisiloxyl (TIPDS).

1. Preparation of starting compound [II']

These starting compounds can be synthesized by applying a known method.

The compounds of formula [II'] can be prepared, for example, by the following reaction process.

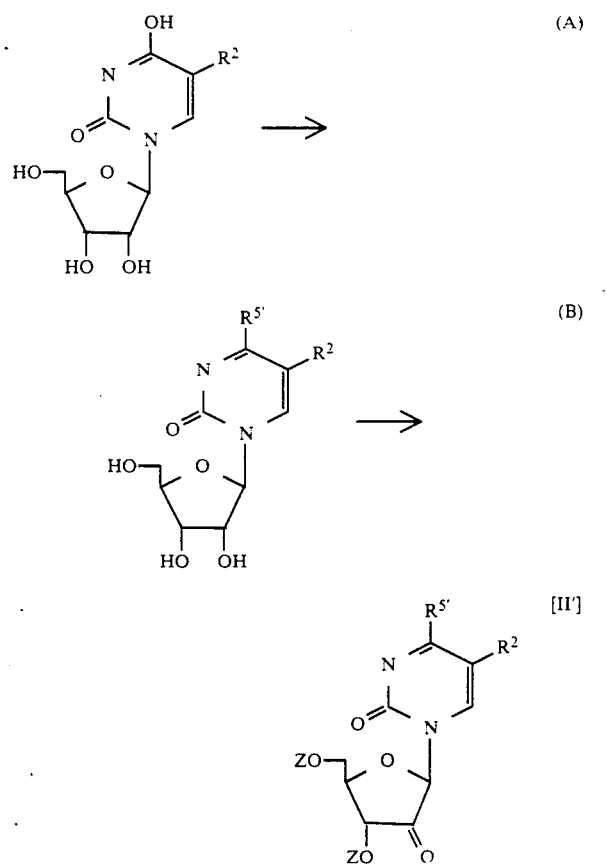

wherein $R^2$, $R^{5'}$ and Z are as defined earlier.

More particularly, the hydroxy groups in the sugar moiety of a uridine derivative of formula (A) are protected, the 4-position in the base moiety is halogenated with a halogenating agent, and then an alkoxy group is introduced at this position by the reaction with an alkoxide to obtain a compound of formula (B). Subsequently, the 3'- and 5'- positions in the sugar moiety of the 4-alkoxy compound of formula (B) thus obtained are protected, and the hydroxy group at the 2'-position in the sugar moiety is subjected to oxidation, whereby a compound of formula [II'] can be obtained.

The hydroxy protecting group in the halogenation reaction is not particularly limited insofar as it does not hinder the halogenation reaction. Conventional hydroxy protecting groups such as acyl groups, acetal- or ketal-type groups, aralkyl groups and silyl groups may be applied, especially preferred protecting groups being those which are not removed due to the presence of an acid such as acyl groups.

The protection with an acyl group, for instance, may be carried out by a conventional method in which the compound of formula (A) is reacted with 3- to 10-fold mols of an acylating agent (e.g., an acid anhydride or acid chloride of acetic acid, propionic acid, butyric acid, benzoic acid, or substituted benzoic acid) in a solvent (e.g., a basic solvent such as pyridine, picoline, diethylaniline, tributylamine and triethylamine or a mixture thereof with acetonitrile, dimethylformamide, dimethylacetamide, formamide, chloroform, methane dichloride, dioxane, tetrahydrofuran or dimethylaminopyridine) at a temperature of from 0° to 50° C.

The halogenation reaction can be carried out by causing a halogenating agent to react with the compound in an inert solvent (e.g., chloroform and methylene chloride). For the halogenating agent, thionyl chloride, thionyl bromide, phosphorus oxychloride and the like, if desired, in the form of a solution in an organic solvent such as dimethyl sulfoxide, can be used.

The amount of the halogenating agent to be added is approximately .1- to 5-fold mols per mol of the compound of formula (A), and the reaction may be carried out under heat at reflux.

The introduction of the alkoxy group can be accomplished by reacting under heat the 4-halogeno-compound of formula (A) with protecting groups with about 1- to 5-fold mols of an alkoxide (e.g., sodium methoxide, potassium methoxide, sodium ethoxide, potassium ethoxide, and sodium propoxide) in a solvent (e.g., methanol, ethanol, and propanol).

The protecting groups at the 3'- and 5'-positions may be those used in the halogenation reaction described above, silyl groups being preferred and TIPDS group being especially preferred.

With reference to the protection, for example, by silylation, the amount of a silylating agent to be used can be suitably determined within the range of from 1- to 3-fold mols per mol of the compound of formula (B), and the same reaction conditions as in the aforementioned acylation reaction can be employed.

As a method for the oxidation of the hydroxy group at the 2'-position, chromic acid oxidation (Method A) using a chromic acid-pyridine-acetic anhydride complex and the like, or activated dimethyl sulfoxide oxidation (Method B) using activated dimethyl sulfoxide obtained from oxalyl chloride-dimethyl sulfoxide and the like can be applied.

The oxidation reaction can be carried out in the presence of an oxidizing agent in an amount of 1- to 10-fold mols per mol of the compound for 1 to 10 hours at $-10°$ C. to room temperature in the case of Method A or at $-10°$ to $-80°$ C. in the case of Method B. 2. Preparation of starting compound [II"]

The compounds of formula [II"] can be prepared, for example, by the following reaction process.

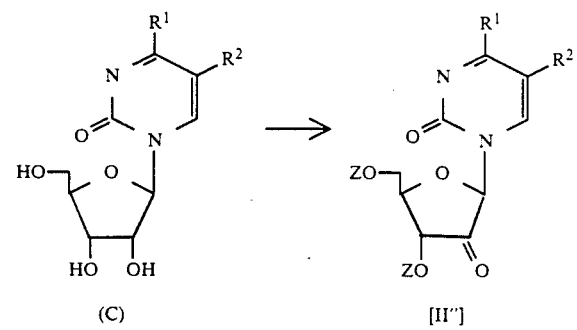

wherein $R^1$, $R^2$ and Z are as defined above.

More particularly, the hydroxy groups at the 3'- and 5'-positions in the sugar moiety of a nucleoside of formula (C) are protected, and thereafter the hydroxy group at the 2'-position in the sugar moiety is subjected to oxidation, whereby a compound of formula [II"] can be obtained.

The protection reaction of the hydroxy groups at the 3'- and 5'-positions and the oxidation reaction of the hydroxy group at the 2'-position can be carried out in accordance with those performed in the preparation of the compound of formula [II'] described above. 3. Preparation of starting compound [II''']

The starting compounds [II'''] can be prepared, for example, by introducing protecting groups on the amino group at the 4-position in the base moiety and the hydroxy groups at the 3'- and 5'-positions in the sugar moiety of a cytidine derivative and then subjecting the hydroxy group at the 2'-position in the sugar moiety to oxidation reaction. This reaction process can be illustrated by the following reaction formulae:

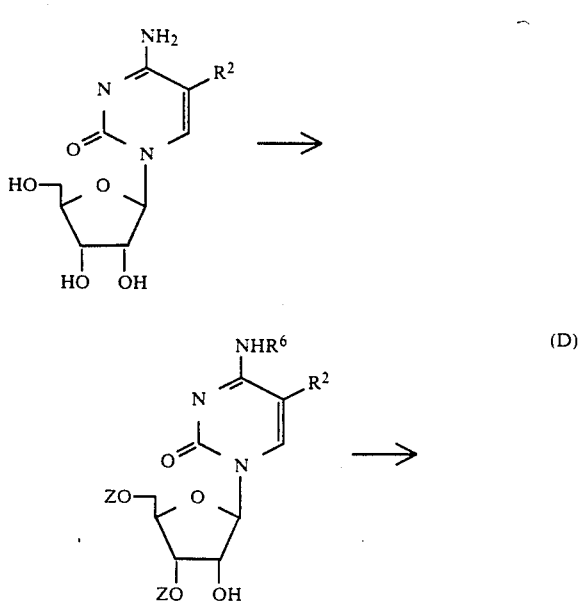

-continued

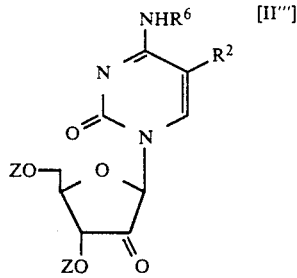

wherein $R^2$, $R^6$ and Z are as defined previously.

The introduction of protecting groups represented by $R^6$ and Z into the cytidine derivative may be carried out in accordance with a method ordinarily employed for the particular protecting groups selected.

For example, an acyl group represented by $R^6$ can be introduced by causing reaction in the presence of 1- to 5-fold mols of an acylating agent (an acid anhydride or acid chloride of the acid corresponding to $R^6$) per mol of the cytidine derivative in a solvent (e.g., a basic solvent such as pyridine, picoline, diethylaniline, tributylamine and triethylamine or a mixture thereof with acetonitrile, dimethylformamide, dimethylacetamide, formamide, chloroform, methane dichloride, dioxane, tetrahydrofuran or dimethylaminopyridine) at a temperature of from 0° to 50° C. for 1 to 30 hours.

Also, a hydroxy protecting group represented by Z, for example, a silyl group, can be introduced by causing reaction in the presence of 1- to 3-fold mols of a silylating agent per mol of the cytidine derivative under the same conditions as in the acylation.

Subsequently, a compound (D) with protecting groups thus prepared is subjected to oxidation reaction to obtain the target starting compound.

The oxidation of the hydroxy group at the 2'-position of the compound (D) can be performed by the aforementioned chromic acid oxidation (Method A) using a chromic acid-pyridine-acetic anhydride complex and the like, or activated dimethyl sulfoxide oxidation (Method B) using activated dimethyl sulfoxide obtained from oxalyl chloride-dimethyl sulfoxide and the like under the conditions described hereinbefore.

The starting compounds [II'], [II"] and [II"'] thus prepared can be isolated and purified by a suitable combination of isolation and purification methods commonly applied to nucleosides (e.g., various chromatographic procedures such as ion exchange and adsorption, and the recrystallization method). For example, after the solvent has been distilled off, the compound is subjected to column chromatography and crystallized from n-hexane or any other suitable organic solvent.

SECOND PROCESS

Step (1) in the second process is the reaction step of alkylidenating the 2'-position in the sugar moiety of the compound of formula [II'] with Wittig's reagent.

The Wittig's reagent used in the alkylidenation reaction is alkylidenephosphorane represented by the formula

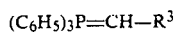

wherein $R^3$ is as defined earlier.

Typically, triphenylphosphine methylene, triphenylphosphine ethylene and triphenylphosphine propylene are employed.

The Wittig's reagent used in the reaction is preferably prepared immediately before use from a triphenylphosphonium compound represented by the formula $[(C_6H_5)_3P^+—CH_2—R^3]X^-$ wherein $R^3$ is as defined earlier and $X^-$ is a halogen ion such as $Br^-$ or $I^-$ (e.g., methyltriphenylphosphonium bromide, methyltriphenylphosphonium iodide, and ethyltriphenylphosphonium bromide) and a strong alkali (e.g., potassium hydride, sodium hydride, n-butyl lithium, sodium methoxide, potassium-t-butoxide, and sodium amide) by a conventional method.

The amount of Wittig's reagent to be used can be suitably determined within the range of from 1- to 3-fold mols per mol of the compound of formula [II'].

The alkylidenation reaction using the above described Wittig's reagent can be carried out by reacting the compound of formula [II'] with Wittig's reagent at -30° to 30° C. for 0.5 to 20 hours in a solvent (e.g. tetrahydrofuran, dioxane, ether, benzene, and dimethyl sulfoxide singly or in a mixture of two or more members).

The compound of formula [III'] thus prepared can be isolated and purified by means of ordinary silica gel column chromatography.

Step (2) in the second process is the reaction step of removing the hydroxy protecting groups in the sugar moiety of the compound of formula [III'].

The removal of the protecting groups may be carried out by suitably selecting an ordinary treatment such as acidic hydrolysis, alkaline hydrolysis, ammonium fluoride treatment or catalytic reduction depending upon the protecting groups used. For example, silyl groups, when used as the hydroxy protecting groups, can be removed by ammonium fluoride treatment or acidic or alkaline hydrolysis.

The compound of formula [IV'] thus synthesized can be isolated by ordinary silica gel column chromatography.

In Step (3) in the second process, the compound of formula [IV'] is subjected to amination reaction in order to obtain the compound of formula [I] in which $R^1$ is an amino group, or hydrolysis reaction in order to obtain the compound of the same formula in which $R^1$ is a hydroxy group.

The amination reaction may be carried out by a conventional method, for example, by reacting methanolic ammonia with the compound of formula [IV'] in a sealed tube. The reaction temperature is 50° to 150° C.

The hydrolysis reaction may also be carried out by a conventional method, especially preferably by acidic hydrolysis.

In order to produce the compound of formula [I] in which $R^4$ is a phosphate residue, the compound of formula [IV'] is reacted, after completion of the amination reaction or the hydrolysis reaction described above, with a phosphorylating agent commonly used for the selective phosphorylation at the 5'-position of nucleosides, such as phosphorus oxychloride or tetrachloropyrophosphoric acid, by a known method, whereby the desired compound can be obtained in the free acid or salt form.

THIRD PROCESS

Step (1) in the third process is the reaction step of alkylidenating the 2'-position in the sugar moiety of the compound of formula [II'] with Wittig's reagent.

The alkylidenation reaction and the isolation and purification of the compound of formula [III"] can be accomplished in accordance with Step (1) in the second process.

Step (2) in the third process is the reaction step of removing the hydroxy protecting groups in the sugar moiety of the compound of formula [III"] and optionally phosphorylating the 5'-position in the sugar moiety thereof.

The removal of the protecting groups and the phosphorylation can be carried out in accordance with Steps (2) and (3) in the second process.

FOURTH PROCESS

Step (1) in the fourth process is the reaction step of alkylidenating the 2'-position in the sugar moiety of the compound of formula [II'''] with Wittig's reagent.

The alkylidenation reaction and the isolation and purification of the compound of formula [III'''] can be accomplished in accordance with Step (1) in the second process.

Step (2) in the fourth process is the reaction step of removing the hydroxy protecting groups in the sugar moiety of the compound of formula [III''']. This removal of the protecting groups and the isolation and purification of the compound of formula [IV'''] can be carried out in accordance with Step (2) in the second process.

Step (3) in the fourth process is the reaction step of removing the acyl group represented by $R^6$ and then optionally phosphorylating the 5'-position in the sugar moiety.

The acyl group can be removed by suitably selecting a removal method customarily used for the particular acyl group employed, for example, by alkaline hydrolysis using a methanol-ammonia (1:1) mixture, concentrated ammonia and the like.

The phosphorylation can be carried out in accordance with that in Step (3) in the second process.

The compound of formula [I] or [I'''] thus synthesized can be isolated and purified by a suitable combination of methods ordinarily employed for the isolation and purification of nucleosides or nucleotides. For example, in the case of a nucleoside ($R^4$ being a hydrogen atom), the compound may be crystallized from an appropriate solvent such as ethanol after the reaction solvent has been distilled off. If desired, the compound can be obtained in salt form. In the case of a nucleotide ($R^4$ being a phosphate residue), on the other hand, the compound is purified by ion exchange column chromatography using an ion exchange resin or by adsorption column chromatography using activated carbon and the like, and freeze-dried or crystallized, whereby the compound in free acid form or, if desired, in salt form can be obtained.

In the event that the phosphonium salt of Wittig's intermediate which is a reaction intermediate (the structure of this intermediate is not clear, but may be presumed to be as shown below in view of the reaction process according to the first process:

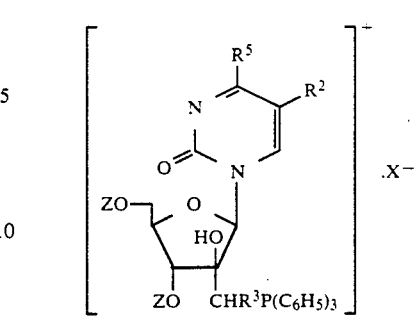

wherein $R^2$, $R^3$, $R^5$, Z and $X^-$ are as defined earlier) remains in the reaction solution in the alkylidenation reaction in the process for producing the compounds of the present invention, i.e., any of the first to fourth processes, the intermediate can optionally be reacted with a strong alkali (e.g., potassium hydride, sodium hydride, n-butyl lithium, sodium methoxide, potassium-t-butoxide, and sodium amide) in a solvent (e.g., tetrahydrofuran, dioxane, ethyl ether, benzene, and dimethyl sulfoxide singly or in a mixture of two or more members) to obtain the compound of formula [III], [III'], [III"] or [III''']. Thus, the production yield of the end product can be increased by carrying out the strong alkali treatment after Step (1) in the respective processes.

The 2'-alkylidenepyrimidine nucleoside derivatives of the present invention can be synthesized by the first process, and more specifically the second to fourth processes, as has been set forth in detail. From those processes, the most suitable one may be selected depending upon the desired compounds and the starting compounds used.

In order to produce, for example, the compound wherein $R^1$ is an amino group, any of the second to fourth processes can be employed, but the fourth process wherein a specific cytidine derivative is used as the starting compound, has the following advantages over the second process wherein a uridine derivative is used as such.

(1) The starting compound supplied for the alkylidenation reaction in the fourth process can be prepared in a shorter reaction step than in the second process.

(2) The fourth process substantially comprises two steps, i.e., the alkylidenation and the removal of protecting groups, and the amination carried out in the second process can be omitted.

(3) The production yield of the end products can be improved by the curtailment or omission of the reaction step as mentioned in paragraphs (1) and (2). More specifically, the overall yield of 2'-alkylidenecytidine derivatives produced from the starting compound 2'-ketonucleoside is 53% in the fourth process and 25% in the second process, indicating that two-fold or more production yield can be attained according to the fourth process.

UTILITY OF THE COMPOUNDS OF THE PRESENT INVENTION

The compounds of the present invention or salts thereof exhibit antiviral activities against DNA viruses such as herpes simplex virus (HSV) and cytomegalovirus (CMV) of the herpesvirus family, and the drugs of the present invention comprising these compounds as active ingredients are clinically used for the treatment of viral infections.

While the dose level of the compounds of the present invention incorporated in the drugs of the present invention as active ingredients may vary depending, for example, upon the severity of patients' diseases and their tolerance for the drugs, and should be determined ultimately by doctors, 0.1 to 10 g, preferably 0.2 to 5 g, per day of the compounds are ordinarily administered to an adult in one portion or several portions. The drugs can be administered in any mode suited for the route of administration.

The drugs of the present invention can be prepared for administration by any conventional method suitable for the purpose. Thus, the drugs include pharmaceutical compositions containing 2'-alkylidenepyrimidine nucleoside derivatives of formula [I] suitable as medicines for humans.

Such compositions are provided for administration by a known method through any pharmaceutically acceptable carriers or adjuvants required.

In the case, for example, of a pharmaceutical composition for oral use, the composition is provided in the form suitable for absorption through the alimentary tract and may be formulated as solid preparations such as tablets, capsules, powders, sugar-coated tablets, and granules, or liquid preparations such as syrups, suspensions and elixirs. The solid preparation can be formulated by selecting and adding from a pharmaceutical viewpoint an adjuvant, for example, a binder such as syrup, gum arabic, gelatin, sorbitol, tragacanth, or polyvinyl pyrrolidone; a vehicle such as lactose, sugar, cornstarch, calcium phosphate, sorbitol, or glycine; a lubricant such as magnesium stearate, talc, polyethylene glycol, or silica; a disintegrator such as potato starch; a wetting agent; a stabilizer; and a taste modifier. For the liquid preparation, a suspending agent such as sorbitol, syrup, methyl cellulose, glucose/sugar syrup, gelatin, hydroxyethyl cellulose, carboxymethyl cellulose, aluminum stearate gel, or a hydrogenated edible fat; an emulsifier; and an antiseptic such as methyl p-hydroxybenzoate, propyl p-hydroxybenzoate, or sorbic acid can be used, if desired, as an adjuvant.

In order to obtain a pharmaceutical preparation for injection use, a pH adjusting agent, a buffer, a stabilizer, a preservative, a solubilizer or the like is added, if desired, to the compounds of the present invention which form active ingredients of the drugs of the invention to formulate a preparation for subcutaneous, intramuscular or intravenous injection by a conventional method.

Hereinafter, the methods for testing the anti-HSV and anti-CMV activities of the compounds of formula [I] incorporated in the drugs of the present invention as active ingredients and the results obtained will be set forth.

TEST METHOD (HSV)

A. Human embryonic lung cells are subcultivated in Eagle's MEM supplemented with 10% semi-fetal calf serum.

B. The cells thus subcultivated are used as a parent culture. A cell suspension obtained from the parent culture by dividing it at 1:2 split is seeded into 96 microwells in an amount of 150 μl/well and incubated in a $CO_2$-incubator at 37° C. for 4 to 5 days.

C. The culture field is discarded, and 100- to 320-50% tissue culture infective doses (100-320 $TCID_{50}$) of HSV type 1 (HSV-1) strain VR-3 or HSV type 2 (HSV-2) strain MS is inoculated. After incubation at 37° C. for 1 hour, the virus fluid is discarded, 150 μl of Eagle's MEM supplemented with 2.5% semi-fetal calf serum and containing an appropriate amount of each test compound is added, and cultivation is carried out at 37° C. Each of the test compounds is usually diluted in the range of from 100 to 1 μg/ml by serial 0.5 $log_{10}$ decrements.

D. After cultivation for 2 to 3 days, the degree of the cytopathic effect (CPE) caused by the viral infection in each of the wells is observed microscopically. At the time when the control cultures, in which the test compound is absent, have shown complete CPE by the viral infection, the degree of CPE in each well is rated from 0 to 4.

E. The minimum concentration at which the CPE is inhibited at least by 50% (indicated by the CPE score not exceeding 2) is defined as the minimum inhibitory concentration (MIC) of the test compound.

TEXT METHOD (CMV)

A. Human embryonic lung cells are subcultivated in Eagle's MEM supplemented with 10% semi-fetal calf serum.

B. The cells thus subcultivated are used as a parent culture. A cell suspension obtained from the parent culture by dividing it at 1:2 split is seeded into 24 semi-microwells in an amount of 150 μl/well and incubated in a $CO_2$-incubator at 37° C. for 4 to 5 days.

C. The culture fluid is discarded, and about 50 plaque forming units of CMV strain AD 169 is inoculated. After incubation at 37° C. for 1 hour, 400 μl of Eagle's MEM supplemented with 2.5% semi-fetal calf serum and containing an appropriate amount of each test compound is added, and cultivation is carried out at 37° C. Each of the test compounds is usually diluted in the range of from 100 to 1 μg/ml by serial 0.5 $log_{10}$ decrements.

D. After cultivation for 4 to 6 days, infected cells are stained with a 0.5% Crystal Violet solution, and the number of plaques formed is counted under the microscope.

E. The minimum concentration at which the plaque formation is inhibited at least by 50%, based on the number of plaques formed in the control cultures in which the test compound is absent, is defined as the minimum inhibitory concentration (MIC) of the test compound.

| Test results: | | | | | | |
|---|---|---|---|---|---|---|
| Test Compound | | | | MIC (μg/ml) | | |
| $R^1$ | $R^2$ | $R^3$ | $R^4$ | HSV-1 | HSV-2 | CMV |
| $NH_2$ | H | H | H | 1 | 1 | 0.1 |
| OH | $CH_3$ | H | H | 1 | 1 | 5.6 |
| OH | Cl | H | H | 10 | 10 | — |
| OH | Br | H | H | 3.2 | 3.2 | — |
| OH | I | H | H | 1 | 1 | — |
| OH | $CH_3$ | $CH_3$ | H | 10 | 32 | — |

EXAMPLE

The present invention will now be illustrated with reference to the following examples, it being understood that these examples are not intended to limit the scope of the invention.

EXAMPLE 1

Preparation of 2'-methylidene-2'-deoxycytidine (compound of formula [I] wherein $R^1$ is $NH_2$, $R^2$ is H, $R^3$ is H, and $R^4$ is H)hydrochloride 1) Synthesis of 4-O-ethyluridine (compound of formula
(B) wherein $R^2$ is H, and $R^{5'}$ is $OC_2H_5$)

To a solution of 3.35 g of 2',3',5'-tri-O-acetyluridine in 50 ml of chloroform were added 8.1 ml of thionyl chloride and 0.5 ml of dimethylformamide, and the mixture refluxed for 6.5 hours and evaporated to dryness under reduced pressure. The residue was dissolved in 20 ml of ethanol and 30 ml of 1N sodium ethoxide added. The mixture was refluxed for 2 hours and neutralized with 1N hydrochloric acid. The salt precipitated was filtered off and the remaining solution concentrated to dryness. The concentrate was adsorbed onto a silica gel column (4×31 cm), a fraction containing the desired compound eluted with a 16% ethanol-chloroform mixture, and the solvent distilled off to obtain the desired compound in crude crystal form. Recrystallization from ethanol gave 2.08 g (yield 84.2%) of the desired compound.

Melting point: 136°–137.5° C.
Elemental analysis:
(as $C_{11}H_{16}N_2O_6 \cdot \frac{1}{3}H_2O$)

| | | |
|---|---|---|
| Calcd. | C: 46.97%, | H: 6.09%, |
| | N: 9.96%, | O: 36.98% |
| Found | C: 46.91%, | H: 6.02%, |
| | N: 9.98%, | O: 37.09% |

2) Synthesis of 1-(3,5-O-TIPDS-β-D-erythropentofuran-2-ulosyl)-4-ethoxy-2-pyrimidinone (compound of formula [II] wherein $R^2$ is H, $R^5$ is $OC_2H_5$, and Z(3')-Z(5') are TIPDS)

To an ice-cooled solution of 7.04 g of 4-O-ethyluridine in 80 ml of pyridine was added 9.57 g of 1,1,3,3-dichlorotetraisopropyldisiloxane, and the mixture stirred at room temperature for 4.5 hours to cause reaction. To the reaction mixture was added ice water, and the solvent distilled off. The residue was partitioned between chloroform and water, the chloroform layer dried and then the solvent distilled off. The residue was adsorbed onto a silica gel column (10×130 cm). Fractions eluted with a 40% ethyl acetate-hexane mixture were collected and concentrated to obtain 12.3 g of a 3',5'-TIPDS compound.

Subsequently, a solution of 2.7 ml of oxalyl chloride in 40 ml of methylene chloride was cooled to −70° C. To the cooled solution was added dropwise over a period of 20 minutes under argon 4.8 ml of dimethyl sulfoxide dissolved in 20 ml of methylene chloride, and the mixture stirred for 30 minutes. To the reaction mixture was added dropwise the above obtained 3',5'-TIPDS compound (12.3 g) dissolved in 50 ml of methylene chloride, the resulting mixture stirred at −70° C. for 2 hours, 20 ml of triethylamine added, and the mixture further stirred for 1 hour. This reaction solution was left standing until its temperature reached room temperature, water added, and the resulting solution partitioned. The methylene chloride layer was removed and the solvent distilled off. The residue was dissolved in ethyl acetate and partitioned from water. The ethyl acetate layer was concentrated to dryness and adsorbed onto a silica gel column (5×28 cm). Fractions eluted with a 20% ethyl acetate-n-hexane mixture and containing the desired compound were collected and the solvent distilled off. The fractions were then crystallized from n-hexane to obtain 10.2 g (yield 72.1%) of the desired compound.

Melting point: 157.5°–159° C.
Elemental analysis:
(as $C_2H_{40}N_2O_7Si_2$)

| | | |
|---|---|---|
| Calcd. | C: 53.87%, | H: 7.86%, |
| | N: 5.46% | |
| Found | C: 53.73%, | H: 7.87%, |
| | N: 5.57% | |

3) Synthesis of 2'-methylidene-4-O-ethyl-2'-deoxyuridine (compound of formula [IV] wherein $R^2$ is H, $R^3$ is H, and $R^5$ is $OC_2H_5$)

232 mg of potassium hydride was added to 2.4 ml of dimethyl sulfoxide under argon and the mixture stirred at room temperature for 40 minutes. The resulting potassium hydride-dimethyl sulfoxide mixture was added dropwise to a solution of 2.2 g of methyltriphenylphosphonium bromide in 8 ml of dimethyl sulfoxide in an ice bath under argon and the mixture stirred for 10 minutes.

To this mixture was added dropwise under argon a solution of 1.02 g of the above obtained crystalline 1-(3,5-O-TIPDS-β-D-erythropentofuran-2-ulosyl)-4-ethoxy-2-pyrimidinone in 10 ml of dimethyl sulfoxide, and the mixture stirred in an ice bath for 2 hours. To the reaction mixture were added 10 ml of 1N aqueous ammonium chloride solution and then 50 ml of ethyl acetate and 40 ml of water whereby the mixture was partitioned. The organic layer was concentrated under reduced pressure, adsorbed onto a silica gel column (2.4×30 cm), and eluted with an n-hexane-ethyl acetate mixture to obtain a 2'-methylidene compound.

To a solution of 320 mg of the thus obtained compound in 10 ml of tetrahydrofuran was added 1 ml of tri-n-butylammonium fluoride, and the mixture stirred at room temperature for 10 minutes. The reaction mixture was neutralized with acetic acid, adsorbed onto a silica gel column (2.4×12 cm), and eluted with a chloroformethanol mixture. Fractions containing the desired compound were collected to obtain 155 mg (yield 30%) of a deprotected 2'-methylidene-4-O-ethyl compound.

Melting point: 157.5°–159° C.
Elemental analysis:
(as $C_{12}H_{16}N_2O_5$)

| | | |
|---|---|---|
| Calcd. | C: 53.72%, | H: 6.01%, |
| | N: 10.44% | |
| Found | C: 53.80%, | H: 5.99%, |
| | N: 10.37% | |

4) Synthesis of 2'-methylidene-2'-deoxycytidine (compound of formula [I] wherein $R^1$ is $NH_2$, $R^2$ is H, $R^3$ is H, and $R^4$ is H)hydrochloride 150 mg of the 2'-methylidene-4-O-ethyl compound was dissolved in 10 ml of an ammonia saturated methanol solution in an ice bath and the resulting solution poured into a tube which was then sealed and heated at 100° C. for 2 days. The reaction solution was allowed to cool, 2 ml of 2N hydrochloric acid added, and the mixture concentrated. Crystallization from an ethanol-water mixture gave 125 mg (yield 81.7%) of the title compound.

Melting point: >300° C. (carbonized at 148°–155° C.)
Elemental analysis:
(as $C_{10}H_{13}N_3O_4 \cdot HCl$)

|  | | |
|---|---|---|
| Calcd. | C: 43.57%, | H: 5.19%, |
| | N: 15.24% | |
| Found | C: 43.47%, | H: 5.23%, |
| | N: 15.22% | |

Example 2

Preparation of 2'-methylidenethymidine (compound of formula [I]
wherein $R^1$ is OH, $R^2$ is $CH_3$, $R^3$ is H, and $R^4$ is H)

1) Synthesis of 3',5'-O-TIPDS-2'-ketothymidine (compound of formula [II] wherein $R^2$ is $CH_3$, and Z(3')-Z(5') are TIPDS)

To a solution of 4.13 g of 5-methyluridine in 50 ml of pyridine was added in an ice bath 5.57 g of 1,1,3,3-dichlorotetraisopropyldisiloxane, and the mixture stirred at room temperature for 6 hours. To the resulting mixture was added a small amount of water, and the mixture stirred for 30 minutes and concentrated to dryness under reduced pressure. The residue was partitioned between chloroform and water, and the organic layer concentrated and adsorbed onto a silica gel column (5×21 cm). From fractions eluted with a 2% ethanol-chloroform mixture was obtained a 3',5'-protected compound.

Separately, a solution of 1.7 ml of oxalyl chloride in 40 ml of methylene chloride was cooled to −70° C. To the cooled solution was added dropwise under argon a solution mixture of 3 ml of dimethyl sulfoxide and 20 ml of methylene chloride, and the resulting mixture stirred for 30 minutes. To the reaction mixture was added dropwise 8.04 g of the above obtained 3',5'-protected compound dissolved in 50 ml of methylene chloride, and the resulting mixture stirred further at −70° C. for 2 hours. To this mixture was added dropwise 6.6 ml of triethylamine, and the solution stirred for 1.5 hours, left standing until its temperature reached room temperature and partitioned between chloroform and water. The organic layer was concentrated to dryness under reduced pressure and developed through a silica gel column (4×28 cm). Fractions eluted with a 40% ethyl acetate-n-hexane mixture were concentrated and crystallized from n-hexane to obtain 6.68 g (yield 83.2%) of a 2'-keto compound.

Melting point: 168°–170° C.
Elemental analysis:
(as $C_{22}H_{38}N_2O_7Si_2$)

|  | | |
|---|---|---|
| Calcd. | C: 52.98%, | H: 7.68%, |
| | N: 5.62% | |
| Found | C: 52.93%, | H: 7.71%, |
| | N: 5.61% | |

2) Synthesis of 2'-methylidenethymidine (compound of formula [I] wherein $R^1$ is OH, $R^2$ is $CH_3$, $R^3$ is H, and $R^4$ is H)

455 mg of potassium hydride was added to 5 ml of dimethyl sulfoxide under argon and the mixture stirred at room temperature for 50 minutes. The resultant solution containing potassium hydride was added dropwise to a separately prepared solution of 4.28 g of methyltriphenylphosphonium bromide in 10 ml of dimethyl sulfoxide in an ice bath, and the mixture stirred further for 20 minutes. To the resultant solution was added dropwise a solution of 1.5 g of the above obtained 3',5'-O-TIPDS-2'-ketothymidine in a solvent mixture of 5 ml of tetrahydrofuran and 5 ml of dimethyl sulfoxide, and the mixture stirred at room temperature for 10 hours.

The reaction solution was then neutralized with 1N ammonium chloride and partitioned between 120 ml of ethyl acetate and 120 ml of water. The organic layer was concentrated to dryness and the residue developed through a silica gel column (2.4×24 cm). Fractions eluted with a 20% ethyl acetate-n-hexane mixture were collected to obtain a 2'-methylidene compound. This compound was dissolved in 10 ml of tetrahydrofuran, 1 ml of 1 M tetra-n-butylammonium fluoride-tetrahydrofuran solution added, and the mixture stirred at room temperature for 10 minutes to deprotect the compound.

Subsequently, the reaction mixture was neutralized with acetic acid, concentrated to dryness under reduced pressure, and developed through a silica gel column 2.4×14 cm). Fractions eluted with a 7% ethanol-chloroform mixture were collected and concentrated to obtain 257 mg (yield 85%) of a crystalline powder of 2'-methylidenethymidine.

Melting point: 161°–162° C.
Elemental analysis:
(as $C_{11}H_{14}N_2O_5$)

|  | | |
|---|---|---|
| Calcd. | C: 49.58%, | H: 5.83%, |
| | N: 11.57% | |
| Found | C: 49.46%, | H: 5.91%, |
| | N: 11.48% | |

EXAMPLE 3

Preparation of 2'-ethylidenethymidine (compound of formula [I] wherein $R^1$ is OH, $R^2$ is $CH_3$, $R^3$ is $CH_3$, and $R^4$ is H)

455 mg of potassium hydride was added to 5 ml of dimethyl sulfoxide under argon and the mixture stirred at room temperature for 50 minutes.

The resultant solution containing potassium hydride was added dropwise to a separately prepared solution of 4.44 g of ethyltriphenylphosphonium bromide in 10 ml of dimethyl sulfoxide in an ice bath and the mixture stirred further for 20 minutes.

To the resulting solution was added dropwise a solution of 1.5 g of the 3',5'-O-TIPDS-2'-ketothymidine obtained in Example 2 in a solvent mixture of 5 ml of tetrahydrofuran and 5 ml of dimethyl sulfoxide, and the mixture stirred at room temperature for 12 hours.

The reaction solution was then neutralized with 1N ammonium chloride and partitioned between 140 ml of ethyl acetate and 140 ml of water. The organic layer was concentrated to dryness and the residue developed through a silica gel column (2×18 cm). Fractions eluted with a 10% ethyl acetate-n-hexane mixture were combined to obtain a 2'-ethylidene compound. This compound was dissolved in 10 ml of tetrahydrofuran, 1 ml of 1 M tetra-n-butylammonium fluoride-tetrahydrofuran solution added, and the mixture stirred at room temperature for 30 minutes to deprotect the compound.

Subsequently, the reaction mixture was neutralized with acetic acid, concentrated to dryness under reduced pressure, and developed through a silica gel column (2×10 cm). Fractions eluted with a 7% ethanol-chloroform mixture were collected and concentrated to obtain 190 mg of an amorphous powder of 2'-ethylidenethymidine.
Elemental analysis:
(as $C_{12}H_{16}N_2O_5$)

| | | |
|---|---|---|
| Calcd. | C: 53.72%, | H: 6.01%, |
| | N: 10.44% | |
| Found | C: 53.68%, | H: 6.15%, |
| | N: 10.39% | |

EXAMPLE 4

Preparation of 2'-methylidene-2'-deoxy-5-fluorouridine (compound of formula [I] wherein $R^1$ is OH, $R^2$ is F, $R^3$ is H, and $R^4$ is H)

1) Synthesis of 1-(3,5-O-TIPDS-β-D-erythropentofuran-2-ulosyl)-5-fluorouracil (compound of formula [II] wherein $R^2$ is F, and Z(3')-Z(5') are TIPDS)

To a solution of 2.42 g of 5-fluorouridine in 30 ml of pyridine was added in an ice bath 3.3 g of 1,1,3,3-dichlorotetraisopropyldisiloxane, and the mixture stirred for 2 hours. The reaction solution was then left standing until its temperature reached room temperature and stirred for 1.5 hours. To the resulting solution was added a small amount of water, and the mixture stirred, concentrated to dryness under reduced pressure, and developed through a silica gel column (2.4×23 cm). Fractions eluted with a 25% ethyl acetate-n-hexane mixture were collected to obtain a 3',5'-O-TIPDS compound.

To a solution of 3.91 g of the 3',5'-O-TIPDS compound in 10 ml of methylene chloride was added 4 equivalents of a chromic acid complex (a mixture of 3 g of chromium trioxide ($CrO_3$), 5 ml of pyridine and 3 ml of acetic anhydride with 80 ml of methylene chloride), and the mixture stirred at room temperature for 1 hour and then at −4° C. for 14 hours. To the resulting mixture was added another 4 equivalents of a chromic acid complex, and the mixture stirred at room temperature for 1 hour. The reaction solution was added dropwise to 600 ml of ethyl acetate and the mixture filtered through silica gel (6×15 cm). The filtrate was concentrated to dryness under reduced pressure and the residue developed through a silica gel column (2.4×21 cm). Fractions eluted with a 20% ethyl acetate-n-hexane mixture were combined to obtain 2.8 g (yield 71.6%) of a 2'-keto compound.

Melting point: 183°–186° C.
Elemental analysis:
(as $C_{21}H_{35}N_2O_7FSi_2$)

| | | |
|---|---|---|
| Calcd. | C: 50.15%, | H: 7.01%, |
| | N: 5.57% | |
| Found | C: 50.01%, | H: 7.22%, |
| | N: 5.49% | |

2) Synthesis of 2'-methylidene-2'-deoxy-5-fluorouridine (compound of formula [I] wherein $R^1$ is OH, $R^2$ is F, $R^3$ is H, and $R^4$ is H)

1.1 g of potassium hydride was added to 12 ml of dimethyl sulfoxide under argon and the mixture stirred for 1 hour.

The resultant solution containing potassium hydride was added dropwise to a separately prepared solution of 11 g of methyltriphenylphosphonium bromide in 25 ml of dimethyl sulfoxide in an ice bath and the mixture stirred further for 10 minutes.

To the resulting solution was added dropwise a solution of 1.4 g of the above obtained 2'-keto compound in 25 ml of dimethyl sulfoxide, and the mixture stirred at room temperature for 10 hours.

The reaction solution was then neutralized with 1N ammonium chloride and partitioned between 200 ml of ethyl acetate and 200 ml of water. The organic layer was concentrated to dryness and the residue developed through a silica gel column (2.4×22 cm). Fractions eluted with a 20% ethyl acetate-n-hexane mixture were collected to obtain a 2'-methylidene compound. This compound was dissolved in 5 ml of tetrahydrofuran, 4 ml of 1 M tetra-n-butylammonium fluoride-tetrahydrofuran solution added, and the mixture stirred at room temperature for 30 minutes to deprotect the compound.

Subsequently, the reaction mixture was neutralized with acetic acid, concentrated to dryness under reduced pressure, and developed through a silica gel column (2.4×17 cm). Fractions eluted with a 7% ethanol-chloroform mixture were combined and concentrated to obtain 0.37 g (yield 54%) of 2'-methylidene-2'-deoxy-5-fluorouridine.

Melting point: 154°–156° C.
Elemental analysis:
(as $C_{10}H_{11}N_2O_5F$)

| | | |
|---|---|---|
| Calcd. | C: 46.55%, | H: 4.30%, |
| | N: 10.86% | |
| Found | C: 46.49%, | H: 4.41%. |
| | N: 10.78% | |

Example 5

Preparation of 2'-methylidene-2'-deoxy-5-iodouridine (compound of formula [I] wherein $R^1$ is OH, $R^2$ is I, $R^3$ is H, and $R^4$ is H)

1) Synthesis of 1-(3,5-O-TIPDS-β-D-erythropentofuran-2-ulosyl)-5-iodouracil (compound of formula [II] wherein $R^2$ is I, and Z(3')-Z(5') are TIPDS)

To a solution of 10.0 g of 5-iodouridine in 100 ml of pyridine was added in an ice bath 8.94 g of 1,1,3,3-dichlorotetraisopropyldisiloxane, and the mixture stirred for 1.5 hours. The reaction solution was then left standing until its temperature reached room temperature and stirred further for 3 hours. To the resulting solution was added a small amount of water, and the mixture stirred, concentrated to dryness under reduced pressure, and developed through a silica gel column (3×30 cm). Fractions eluted with a 25% ethyl acetate-n-hexane mixture were collected to obtain a 3',5'-O-TIPDS compound.

To a solution of 13.65 g of the 3',5'-O-TIPDS compound in 30 ml of methylene chloride was added 4 equivalents of a chromic acid complex (a mixture of 9 g of chromium trioxide ($CrO_3$), 15 ml of pyridine and 9 ml of acetic anhydride with 230 ml of methylene chloride), and the mixture stirred at room temperature for 2 hours. To the resulting mixture was further added 2 equivalents of a chromic acid complex, and the mixture stirred at room temperature for another 2 hours. The reaction solution was then added dropwise to 1.5 liters of ethyl acetate and the mixture filtered through silica gel (10×20 cm). The filtrate was concentrated to dryness under reduced pressure and the residue developed through a silica gel column (3.0×32 cm). Fractions eluted with a 20% ethyl acetate-n-hexane mixture were collected to obtain 4.4 g of a 2'-keto compound.

2) Synthesis of 2'-methylidene-2'-deoxy-5-iodouridine (compound of formula [I] wherein $R^1$ is OH, $R^2$ is I, $R^3$ is H, and $R^4$ is H)

To a solution of 22.0 g of methyltriphenylphosphonium bromide in 100 ml of tetrahydrofuran was added dropwise under argon 37.5 ml of n-butyllithium, and the mixture stirred for 1 hour.

To this solution was added dropwise at −10° C. a solution of 4.0 g of the above obtained 2'-keto compound in 20 ml of tetrahydrofuran, and the mixture stirred at this temperature for 30 minutes and then at room temperature for 1.5 hours.

Subsequently, the reaction solution was neutralized with 1N ammonium chloride and partitioned between 200 ml of ethyl acetate and 200 ml of water. The organic layer was concentrated to dryness and the residue developed through a silica gel column (3×23 cm). Fractions eluted with a 20% ethyl acetate-n-hexane mixture were collected to obtain a 2'-methylidene compound.

To a solution of 300 mg of the thus obtained 2'-methylidene compound in 5 ml of tetrahydrofuran was added 1.1 ml of 1 M tetra-n-butylammonium fluoride-tetrahydrofuran solution, and the mixture stirred at room temperature for 30 minutes to deprotect the compound.

The reaction mixture was thereafter neutralized with acetic acid, concentrated to dryness under reduced pressure, and developed through a silica gel column (2.4×17 cm). Fractions eluted with a 7% ethanol-chloroform mixture were collected and concentrated to obtain 118 mg of 2'-methylidene-2'-deoxy-5-iodouridine.

Melting point 169°–172° C.
Elemental analysis:
(as $C_{10}H_{11}N_2O_5I$)

| Calcd. | C: 32.82%, | H: 3.03%, |
|---|---|---|
|  | N: 7.65% |  |
| Found | C: 32.76%, | H: 3.15%, |
|  | N: 7.60% |  |

EXAMPLE 6

Preparation of 2'-methylidene-2-'-deoxy-5-bromouridine (compound of formula [I] wherein $R_1$ is OH, $R^2$ is Br, $R^3$ is H, and $R^4$ is H)

To a solution of 3.32 g of 5-bromouridine in 30 ml of pyridine was added in an ice bath 3.3 g of 1,1,3,3-dichlorotetraisopropyldisiloxane, and the mixture stirred for 2 hours. The reaction solution was left standing until its temperature reached room temperature and stirred for an additional 1': hours. To the resulting solution was added a small amount of water, and the mixture stirred, concentrated to dryness under reduced pressure, and developed through a silica gel column (2.4×25 cm). Fractions eluted with a 25% ethyl acetate-n-hexane mixture were collected to obtain a 3',5'-O-TIPDS compound.

To a solution of 4.30 g of the 3',5'-O-TIPDS compound in 10 ml of methylene chloride was added 4 equivalents of a chromic acid complex (a mixture of 3 g of chromium trioxide ($CrO_3$), 5 ml of pyridine and 3 ml of acetic anhydride with 80 ml of methylene chloride), and the mixture stirred at room temperature for 2 hours.

The reaction solution was then added dropwise to 300 ml of ethyl acetate and the mixture filtered through silica gel (6×10 cm). The filtrate was concentrated to dryness under reduced pressure and the residue developed through a silica gel column (2.4×32 cm). Fractions eluted with a 20% ethyl acetate-n-hexane mixture were collected to obtain 2.4 g of a 2'-keto compound.

To a solution of 3.3 g of methyltriphenylphosphonium bromide in 20 ml of tetrahydrofuran was added dropwise under argon in an ice bath 6.6 ml of n-butyllithium, and the mixture stirred further for 50 minutes.

To the resulting solution was added dropwise at −10° C. a solution of 650 mg of the above obtained 2'-keto compound in 10 ml of tetrahydrofuran, and the mixture stirred at this temperature for 1 hour and then at room temperature for 4 hours.

Subsequently, the reaction solution was neutralized with 1N ammonium chloride and partitioned between 100 ml of ethyl acetate and 100 ml of water. The organic layer was concentrated to dryness and the residue developed through a silica gel column (2.4×18 cm). Fractions eluted with a 20% ethyl acetate-n-hexane mixture were combined to obtain a 2'-methylidene compound. This compound was dissolved in 5 ml of tetrahydrofuran, 1.4 ml of 1 M tetra-n-butylammonium fluoride-tetrahydrofuran solution added, and the mixture stirred at room temperature for 30 minutes to deprotect the compound.

The reaction mixture was then neutralized with acetic acid, concentrated to dryness under reduced pressure, and developed through a silica gel column (2.4×12 cm). Fractions eluted with a 7% ethanol-chloroform mixture were collected and concentrated to obtain 2'-methylidene-2'-deoxy-5-bromouridine as an amorphous powder.

Elemental analysis:
(as $C_{10}H_{11}N_2O_5Br$)

| Calcd. | C: 37.65%, | H: 3.48%, |
|---|---|---|
|  | N: 8.78% |  |
| Found | C: 37.49%, | H: 3.55%, |
|  | N: 8.79% |  |

EXAMPLE 7

Preparation of 2'-methylidene-2'-deoxy-uridine (compound of formula [I] wherein $R^1$ is OH, $R^2$ is H, $R^3$ is H, and $R^4$ is H)

To a solution of 3.91 g of uridine in 50 ml of pyridine was added in an ice bath 5.57 g of 1,1,3,3-dichlorotetraisopropyldisiloxane, and the mixture stirred at room temperature for 6 hours. To the resulting solution was added a small amount of water, and the mixture stirred for 30 minutes and concentrated under reduced pressure. The residue was partitioned between chloroform and water, and the organic layer concentrated and adsorbed onto a silica gel column (5×21 cm). From fractions eluted with a 2% ethanol-chloroform mixture was obtained a 3',5'-protected compound.

Separately, a solution of 1.7 ml of oxalyl chloride in 40 ml of methylene chloride was cooled to −70° C. To the cooled solution was added dropwise under argon a solution mixture of 3 ml of dimethyl sulfoxide and 20 ml of methylene chloride, and the resulting mixture stirred for 30 minutes. To the reaction solution was added dropwise a solution of 7.8 g of the above obtained 3',5'-protected compound in 50 ml of methylene chloride, and the mixture stirred further at −70° C. for 2 hours. To the resulting solution was added dropwise 6.6 ml of triethylamine, and the mixture stirred for 1.5 hours. The reaction solution was then left standing until its temperature reached room temperature and partitioned between chloroform and water. The organic layer was concentrated to dryness under reduced pressure and developed through a silica gel column (4×28 cm). Fractions eluted with a 40% ethyl acetate-n-hexane mixture were concentrated and crystallized from n-hexane to obtain 6.53 g of a 2'-keto compound.

Separately, to a solution of 22.0 g of methyltriphenylphosphonium bromide in 100 ml of tetrahydrofuran was added dropwise under argon 37.5 ml of n-butyllithium, and the mixture stirred for 1 hour. To the resulting solution was added dropwise at −10° C. a solution of 3.2 g of the above obtained 2'-keto compound in 20 ml of tetrahydrofuran, and the mixture stirred at this temperature for 30 minutes and then at room temperature for 1.5 hours.

The reaction solution was thereafter neutralized with 1N ammonium chloride and partitioned between 200 ml of ethyl acetate and 200 ml of water. The organic layer was concentrated to dryness and the residue developed through a silica gel column (3×24 cm). Fractions eluted with a 20% ethyl acetate-n-hexane mixture were collected to obtain a 2'-methylidene compound.

240 mg of the thus obtained 2'-methylidene compound was dissolved in 5 ml of tetrahydrofuran, 1 ml of 1 M tetra-n-butylammonium fluoride-tetrahydrofuran solution added, and the mixture stirred at room temperature for 30 minutes to deprotect the compound.

The reaction mixture was then neutralized with acetic acid, concentrated to dryness under reduced pressure, and developed through a silica gel column (2.4×14 cm). Fractions eluted with a 7% ethanol-chloroform mixture were collected and concentrated to obtain 77 mg of a crystalline powder of 2'-methylidene-2'-deoxy-uridine.

Melting point: 163°–165° C.
Elemental analysis:
(as $C_{10}H_{12}N_2O_5$)

| Calcd. | C: 50.00%, | H: 5.04%, |
|---|---|---|
| | N: 11.66% | |
| Found | C: 49.88%, | H: 5.13%, |
| | N: 11.59% | |

EXAMPLE 8

Preparation of 2'-methylidene-2'-deoxy-5-chlorouridine (compound of formula [I] wherein $R^1$ is OH, $R^2$ is Cl, $R^3$ is H, and $R^4$ is H)

Protection, oxidation, methylidenation and deprotection reactions were carried out similarly as in Example 7 except that the uridine was replaced by 5-chlorouridine to obtain 2'-methylidene-2'-deoxy-5-chlorouridine.

In this example, the 40% ethyl acetate-n-hexane mixture was also replaced by a 30% ethyl acetate-n-hexane mixture.

Melting point: 149°–152° C.
Elemental analysis:
(as $C_{10}H_{11}N_2O_5Cl$)

| Calcd. | C: 43.68%, | H: 4.03%, |
|---|---|---|
| | N: 10.19% | |
| Found | C: 43.77%, | H: 3.98%. |
| | N: 10.20% | |

EXAMPLE 9

Preparation of 2'-methylidenethymidine-5'-phosphoric acid

To an ice-cooled solution of 2.54 g of 2'-methylidenethymidine in 60 ml of trimethylphosphoric acid was added dropwise 1.53 g of phosphorus oxychloride, and the mixture stirred for 1 hour. The reaction solution was poured into 100 ml of ice-cooled water containing 8 g of sodium hydrogencarbonate, and the mixture stirred for 1 hour. Then 100 ml of ether was added, and the resulting solution partitioned. The aqueous layer was concentrated, adsorbed onto an anion exchange resin, Dowex 1 (Formic Acid Type), and eluted with 1 M formic acid solution. Fractions containing the desired compound were combined, concentrated, and freeze-dried to obtain 2'-methylidenethymidine-5'-phosphoric acid.

EXAMPLE 10

Preparation of 2'-deoxy-2'-methylidenecytidine (compound of formula [I] wherein $R^1$ is $NH_2$, $R^2$ is H, $R^3$ is H, and $R^4$ is H)hydrochloride 1) Synthesis of 3',5'-O-(tetraisopropyldisiloxane-1,3-diyl)-4-N-benzoylcytidine (compound of formula [D] wherein $R^2$ is H, $R^6$ is $COC_6H_5$, and Z(3')-Z(5') are TIPDS)

To a solution of 5 g (20.6 mmol) of 4-N-benzoylcytidine in 50 ml of pyridine was added 7.1 ml (22.6 mmol) of 1,1,3,3-dichlorotetraisopropyldisiloxane, and the mixture stirred at 0° C. for 3 hours and subsequently at room temperature for 3 hours to cause reaction. After completion of the reaction, ice water was added to the reaction solution and the solvent distilled off under reduced pressure. The residue was dissolved in ethyl acetate and partitioned three times from water. The organic layer was dried over sodium sulfate anhydride and the solvent distilled off under reduced pressure. The residue was adsorbed onto a silica gel column (5×10 cm) and eluted with a 33% ethyl acetate-hexane solvent mixture to obtain fractions containing the desired compound. These fractions were concentrated under reduced pressure to obtain 7.3 g (yield 86%) of an amorphous powder of 3',5'-O-(tetraisopropyldisiloxane-1,3-diyl)-4-N-benzoylcytidine.

Elemental analysis:
(as $C_{28}H_{43}N_3O_7Si \cdot H_2O$)

| Calcd. | C: 55.32%, | H: 7.46%, |
|---|---|---|
| | N: 6.91% | |
| Found | C: 55.54%, | H: 7.41%, |
| | N: 6.99% | |

2) Synthesis of 3'5'-O-(tetraisopropyldisiloxane-1,3-diyl)-2'-keto-4-N-benzoylcytidine (compound of formula [II] wherein $R^2$ is H, $R^5$ is $NHCOC_6H_5$, and Z(3')-Z(5') are TIPDS)

5 g (40 mmol) of chromium trioxide ($CrO_3$), 8.3 ml (80 mmol) of pyridine and 5 ml (40 mmol) of acetic anhydride were dissolved together in 110 ml of methylene chloride to prepare a chromic acid complex solution. In this solution was dissolved 5.9 g (10 mmol) of 3',5'-O-(tetraisopropyldisiloxane-1,3-diyl)-4-N-benzoylcytidine, and the solution stirred at room temperature for 1 hour to cause reaction. After completion of the reaction, 500 ml of ethyl acetate was added dropwise to the reaction solution and the mixture passed through a silica gel column (6×1.5 cm) to obtain filtrates. The filtrates collected were evaporated to dryness under reduced pressure. The residue was adsorbed onto a silica gel column (3.0×21 cm), eluted with a 25% ethyl acetate-hexane solvent mixture, and crystallized from ethyl acetate-hexane to obtain 4.6 g (yield 78%) of 3',5'-O-(tetraisopropyldisiloxane-1,3-diyl)-2'-keto-4-N-benzoylcytidine.

Melting point: 135°–137° C.
Elemental analysis:
(as $C_{28}H_{41}N_3O_7Si_2$)

| Calcd. | C: 57.21%, | H: 7.03%, |
|---|---|---|
|  | N: 7.15% |  |
| Found | C: 57.08%, | H: 7.12%, |
|  | N: 7.01% |  |

3) Synthesis of 3',5'-O-(tetraisopropyldisiloxane-1,3-diyl)-2'-deoxy-2'-methylidene-4-N-benzoylcytidine (compound of formula [III] wherein $R^2$ is H, $R^3$ is H, $R^5$ is $NHCOC_6H_5$, and Z(3')-Z(5') are TIPDS)

To a suspension of 10.7 g (30 mmol) of methyltriphenylphosphonium bromide in 60 ml of tetrahydrofuran cooled to −20° C. was added dropwise 15.8 ml (25 mmol) of an n-butyllithium solution, and the mixture stirred for 1 hour to cause reaction. To the resulting solution was added dropwise a solution of 2.9 g (5 mmol) of 3',5'-O-(tetraisopropyldisiloxane-1,3-diyl)-2'-keto-4-N-benzoylcytidine in 20 ml of tetrahydrofuran, and the mixture caused to react at −20° C. for 1 hour. The reaction solution was left standing until its temperature reached room temperature and stirred for a further 2 hours to cause reaction. After completion of the reaction, 50 ml of 1N aqueous solution of ammonium bromide was added to the reaction solution. Ethyl acetate was added, and the mixture partitioned. The organic layer was washed twice with water and dried over sodium sulfate anhydride, and the solvent distilled off under reduced pressure. The residue was adsorbed onto a silica gel column (2.4×20 cm) and eluted with a 25% ethyl acetate-hexane solvent mixture to obtain 0.9 g of an amorphous powder of 3',5'-O-(tetraisopropyldisiloxane-1,3-diyl)-2'-deoxy-2'-methylidene-4-N-benoylcytidine.

Furthermore, fractions eluted with a 6.25% ethanol-dichloromethane mixture in the above-mentioned silica gel column were collected and concentrated to dryness. The residue was dissolved in 35 ml of tetrahydrofuran, 6.1 g of a 60% powdery reagent of sodium hydride added under argon, and the mixture stirred at room temperature for 3 hours. In the same manner as was described above, an aqueous solution of ammonium bromide was added to the reaction solution, and the mixture partitioned between ethyl acetate and water and further purified through a silica gel column to obtain 1.2 g (2.1 g in total, yield 72%) of an amorphous powder of 3',5'-O-(tetraisopropyldisiloxane-1,3-diyl)-2'-deoxy-2'-methylidene-4-N-benzoylcytidine.

Elemental analysis:
(as $C_{29}H_{43}N_3O_6Si_2$)

| Calcd. | C: 59.46%, | H: 7.40%, |
|---|---|---|
|  | N: 7.17% |  |
| Found | C: 59.39%, | H: 7.52%, |
|  | N: 7.10% |  |

4) Synthesis of 2'-deoxy-2'-methylidene-4-N-benzoylcytidine (compound of formula [IV] wherein $R^2$ is H, $R^3$ is H, and $R^5$ is $NHCOC_6H_5$)

To a solution of 343 mg (1 mmol) of 3',5'-O-(tetraisopropyldisiloxane-1,3-diyl)-2'-deoxy-2'-methylidene-4-N-benzoylcytidine in 10 ml of tetrahydrofuran was added 2.2 ml of 1N tributylammonium fluoride, and the mixture stirred at 0° C. for 30 minutes to cause reaction. The reaction solution was neutralized with acetic acid and the solvent distilled off under reduced pressure. The residue was developed through a silica gel column (1.6×30 cm, 8% ethanol-chloroform being used as a solvent for elution) and crystallized from ethyl ether-ethanol to obtain 302 mg (yield 88%) of 2'-deoxy-2'-methylidene-4-N-benzoylcytidine.

Melting point: >300° C.
Elemental analysis:
(as $C_{17}H_{17}N_3O_5$)

| Calcd. | C: 59.47%, | H: 4.99%, |
|---|---|---|
|  | N: 12.24% |  |
| Found | C: 59.28%, | H: 5.05%, |
|  | N: 12.11% |  |

Synthesis of 2'-deoxy-2'-methylidenecytidine (Compound of formula [I] wherein $R^1$ is $HN_2$, $R^2$ is H, $R^3$ is H, and $R^4$ is H)hydrochloride A solution of 139 mg (0.5 mmol) of 2'-deoxy-2'-methylidene-4-N-benzoylcytidine in 10 ml of methanolic ammonia was stirred at room temperature for 6 hours to cause reaction and the solvent distilled off under reduced pressure. The residue was developed through a silica gel column (1.6×10 cm, 20% ethanol-chloroform being used as a solvent for elution), fractions containing the desired compound collected, 2 ml of 1N hydrochloric acid added, and the solvent distilled off under reduced pressure. The residue was crystallized from acetone-methanol to obtain 115 mg (yield 83%) of 2'-deoxy-2'-methylidenecytidine.

EXAMPLE 11

| Tablet | |
|---|---|
| 2'-Methylidenethymidine | 10 g |
| Cornstarch | 65 g |
| Carboxycellulose | 20 g |
| Polyvinyl pyrrolidone | 3 g |
| Calcium stearate | 2 g |
| Total | 100 g |

Tablets each weighing 100 mg and containing 10 mg of 2'-methylidenethymidine are prepared by a conventional method.

EXAMPLE 12

| Powder & Capsule | |
|---|---|
| 2'-Methylidene-2'-deoxycytidine hydrochloride | 20 g |
| Crystalline cellulose | 80 g |

-continued

| Powder & Capsule | |
|---|---|
| | Total 100 g |

The two substances in powder form are blended together to formulate a powder.

Further, 100 mg of the powder is charged into a No. 5 hard capsule to prepare capsules.

INDUSTRIAL APPLICABILITY

As has been set forth hereinabove, the novel compounds of the present invention, 2'-alkylidenepyrimidine nucleoside derivatives or salts thereof, exhibit remarkable antiviral activity, especially against herpes simplex virus (HSV) and cytomegalovirus (CMV), and therefore drugs comprising these compounds as active ingredients are useful as antiviral agents.

We claim:

1. A 2'-alkylidenepyrimidine nucleoside derivative represented by formula:

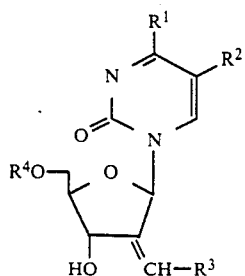

[I]

wherein $R^1$ is an amino or hydroxy group, $R^2$ is a hydrogen or halogen atom or a lower alkyl group of 1 to 8 carbon atoms, $R^3$ is a hydrogen atom or a lower alkyl group of 1 to 8 carbon atoms, and $R^4$ is a hydrogen atom or a phosphate moiety, or a salt thereof.

2. The 2'-alkylidenepyrimidine nucleoside derivative or salt thereof as claimed in claim 1, wherein $R^3$ is a hydrogen atom.

3. The 2'-alkylidenepyrimidine nucleoside derivative or salt thereof as claimed in claim 1, wherein $R^2$ is a hydrogen or halogen atom or a methyl group, and $R^3$ is a hydrogen atom.

4. The 2'-alkylidenepyrimidine nucleoside derivative or salt thereof as claimed in claim 1, wherein $R^1$ is an amino group, and $R^2$ and $R^3$ each are a hydrogen atom.

5. The 2'-alkylidenepyrimidine nucleoside derivative or salt thereof as claimed in claim 1, wherein $R^1$ is a hydroxy group, $R^2$ is a methyl group, and $R^3$ is a hydrogen atom.

6. An antiviral agent comprising an antivirally effective amount of a 2'-alkylidenepyrimidine nucleoside derivative of formula:

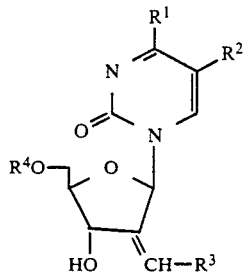

[I]

wherein $R^1$ is an amino or hydroxy group, $R^2$ is a hydrogen or halogen atom or a lower alkyl group of 1 to 8 carbon atoms, $R^3$ is a hydrogen atom or a lower alkyl group of 1 to 8 carbon atoms, and $R^4$ is a hydrogen atom or a phosphate moiety, or a salt thereof, and a pharmaceutically acceptable carrier or adjuvant.

7. The antiviral agent as claimed in claim 6, wherein the virus is a DNA virus.

8. The antiviral agent as claimed in claim 6, wherein the virus is a DNA virus of the herpesvirus family.

9. The antiviral agent as claimed in any of claims 6, 7 and 8, wherein $R^3$ is a hydrogen atom.

10. The antiviral agent as claimed in any of claims 6, 7 and 8, wherein $R^2$ is a hydrogen or halogen atom or a methyl group, and $R^3$ is a hydrogen atom.

11. A method for the treatment of viral infections of the herpesvirus family in a subject, which comprises administering to said subject, a therapeutically effective amount of an antiviral agent comprising an antivirally effective amount of a 2'-alkylidenepyrimidine nucleoside derivative of formula:

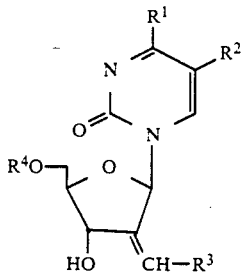

[I]

wherein $R^1$ is an amino or hydroxy group, $R^2$ is a hydrogen or halogen atom or a lower alkyl group of 1 to 8 carbon atoms, $R^3$ is a hydrogen atom or a lower alkyl group of 1 to 8 carbon atoms, and $R^4$ is a hydrogen atom or a phosphate moiety, or a salt thereof, and a pharmaceutically acceptable carrier or adjuvant.

* * * * *